United States Patent
Ciamillo et al.

(10) Patent No.: US 8,088,089 B2
(45) Date of Patent: Jan. 3, 2012

(54) APPARATUS AND METHODS FOR REDUCING SHOULDER DISLOCATIONS

(76) Inventors: Louis P Ciamillo, North Augusta, SC (US); Matthew Lyon, North Augusta, SC (US)

( * ) Notice: Subject to any disclaimer, the term of this patent is extended or adjusted under 35 U.S.C. 154(b) by 180 days.

(21) Appl. No.: 12/361,753

(22) Filed: Jan. 29, 2009

(65) Prior Publication Data
US 2009/0192426 A1 Jul. 30, 2009

Related U.S. Application Data

(60) Provisional application No. 61/024,421, filed on Jan. 29, 2008.

(51) Int. Cl.
*A61F 5/00* (2006.01)
(52) U.S. Cl. ............. 602/20; 602/13; 128/DIG. 20
(58) Field of Classification Search ........... 602/4, 5, 602/13, 20–22; 128/878–879, DIG. 20
See application file for complete search history.

(56) References Cited

U.S. PATENT DOCUMENTS

| | | | | |
|---|---|---|---|---|
| 4,258,441 A | * | 3/1981 | Bell | 623/64 |
| 5,171,310 A | * | 12/1992 | Chisena | 602/5 |
| 5,423,333 A | * | 6/1995 | Jensen et al. | 128/878 |
| 5,569,172 A | * | 10/1996 | Padden et al. | 602/20 |
| 5,810,750 A | * | 9/1998 | Buser | 602/13 |
| 6,179,799 B1 | * | 1/2001 | Doran | 602/20 |
| 2004/0181156 A1 | * | 9/2004 | Kingsford et al. | 600/490 |

* cited by examiner

*Primary Examiner* — Michael A. Brown
(74) *Attorney, Agent, or Firm* — Ballard Spahr LLP

(57) ABSTRACT

The present invention is directed to apparatus, systems, and methods for reducing anterior shoulder dislocations in a patient. In one embodiment, the apparatus of the present invention comprises a humeral cuff, an inflatable bladder, a source of pressurized gas in select fluid communication with the inflatable bladder, and at least one elongated belt attached to the humeral cuff. In another embodiment, the system of the present invention comprises the apparatus of the present invention and at least one weight configured to selectively couple to at least a portion of the at least one elongated belt. In a further embodiment, the methods of the present invention comprise positioning the patient in a substantially prone position, providing the system of the present invention, selectively positioning the humeral cuff in an operative position, and attaching at least one weight to at least one elongated belt such that downward graviational force is applied to the patient's arm to effect the desired reduction.

14 Claims, 2 Drawing Sheets

APPARATUS AND METHODS FOR REDUCING SHOULDER DISLOCATIONS

This application claims priority to U.S. Provisional Application No. 61/024,421, filed on Jan. 29, 2008, which is incorporated in its entirety in this document by reference.

FIELD OF THE INVENTION

The application is related to an orthopedic apparatus and a method of using the same. In particular, the invention is directed toward an apparatus and method for the reduction of anterior dislocations in shoulders.

BACKGROUND

Early treatment of a shoulder dislocation eliminates the stretch and compression of nerves and muscle, and reduces the amount of muscle spasm that must be overcome to reduce the shoulder. Although some dislocations may be reduced without medication, in many instances, the patient is lightly anaesthetized or given a muscle relaxant. The administration of pain medication and/or the depth of anesthesia depends on the amount of trauma that produced the dislocation, the duration of the dislocation, how many times the patient has previously dislocated, whether the dislocation is locked, and to what extent the patient can voluntarily relax his shoulder muscles.

There are several techniques for reduction of a shoulder dislocation, which include: leverage methods, such as Hippocrates' technique and Kocher's technique; Stimson's technique; Milch's Technique; traction-countertraction methods, including Matsen's preferred method; and scapular manipulation.

Kocher's technique was first described in Egyptian hieroglyphs 3,000 years ago. For this maneuver, the humeral head is levered on the anterior surface of the shoulder cavity and the long shaft of the humerus is levered against the chest wall until the reduction is complete. Hippocrates' technique is useful when only one person is available to reduce the shoulder. In this technique, longitudinal traction of the arm is performed and countertraction is applied to the axilla, usually with the heel of the foot of the physician. The traction of the arm is slow and gentle, and the arm may be gently rotated internally and externally to disengage the head of the humerus. Leverage methods, such as Kocher's and Hippocrates' techniques, are often discouraged because of the increased incidence of humeral shaft fractures, injuries to the shoulder capsule, and axillary nerve damage.

Using Stimson's Technique, a patient lies prone on a bed or table with the dislocated arm hanging over the edge of the bed or table. Traction is provided by appropriate weight (e.g., 5 pounds) attached to the wrist of the dislocated arm, which hangs free over the edge of the table. The weighted arm dangles, placing constant traction on the shoulder, which gradually overcomes the muscle spasm. Analgesia and/or muscle relaxation is also recommended for use with this technique. Reduction of a dislocated shoulder using the Stimson technique usually requires 15 to 30 minutes; however, if reduction does not occur spontaneously, reduction may be achieved by rotating the arm internally and externally to disengage the head of the humerus.

Milch's Technique requires a physician to abduct the dislocated arm of the patient with one hand while applying pressure to the humeral head with the other hand. When the patient's arm is fully abducted, external rotation and traction are applied, and the head of the humerus is gently pushed back into place. A modified version of this technique may also be performed with the patient in the prone position.

The traction-countertraction method requires two practitioners. One practitioner applies axial traction to the dislocated arm by pulling the affected limb down and laterally at approximately 45 degrees. A second practitioner applies countertraction using a sheet wrapped under the arm and around the chest while the shoulder is gently rotated internally and externally by the first practitioner to disengage the humeral head from the glenoid.

Matsen's preferred method of anterior reduction also utilizes a form of traction-countertraction. As the patient lies supine, a sheet is wrapped around the patient's chest, which is then wrapped around one practitioner's waist for countertraction. A second practitioner stands on the side of the dislocated shoulder near the patient's waist with the elbow of the dislocated shoulder bent to 90 degrees. A second sheet, tied loosely around the second practitioner's waist and looped over the patient's forearm, provides traction while the second practitioner leans back against the sheet while grasping the forearm. Steady traction along the axis of the arm usually causes reduction.

In scapular manipulation, the patient sits upright, and one practitioner provides forward traction on the dislocated arm. A second operator approached the patient from behind and manipulates the scapula by pivoting it clockwise for a right shoulder and counter clockwise for a left shoulder. This is performed by rotating the inferior tip of the scapula medially with both thumbs while supporting the top of the scapula. An alternative method of performing scapular manipulation involves the patient lying prone with forward traction provided by weights (e.g. 5 lbs) attached to the wrist of the affected arm, as in Stimson's technique. The scapula is then manipulated in the same fashion.

Additional simple techniques for reducing the dislocated shoulder also exist, including: the forward elevation maneuver, the modified gravity method, the crutch and chair technique, the chair and pillow technique, the external rotation method, and the snowbird reduction technique, among others.

Though these techniques are useful, it remains desirable to provide systems, methods, and apparatus for reducing a dislocated shoulder that do not require an intact lower arm or multiple people to reduce the shoulder.

SUMMARY

In one embodiment of the present invention, a system for reducing anterior shoulder dislocations in a patient can include a humeral cuff that defines an internal compartment and is configured to selectively substantially surround a select portion of the patient's arm. The system can also include an inflatable bladder mounted inside the internal compartment of the humeral cuff and at least one elongated belt that is connected to the humeral cuff. In operation, weights can be selectively coupled to at least a portion of the one or more elongated belts to effect the application of pressure to the patient's arm to effect the desired reduction.

Related systems, methods, and apparatus of operation are also provided. Other systems, methods, apparatus, features, and advantages of the invention will be or become apparent to one with skill in the art upon examination of the following figures and detailed description. It is intended that all such additional systems, methods, apparatus, features, and advantages be included within this description, be within the scope of the invention, and be protected by the accompanying claims.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. Those skilled in the relevant art will recognize that many changes can be made to the embodiments described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "bore" includes aspects having two or more bores unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of embodiments of the invention and to the Figures and their previous and following description.

Figure 1:
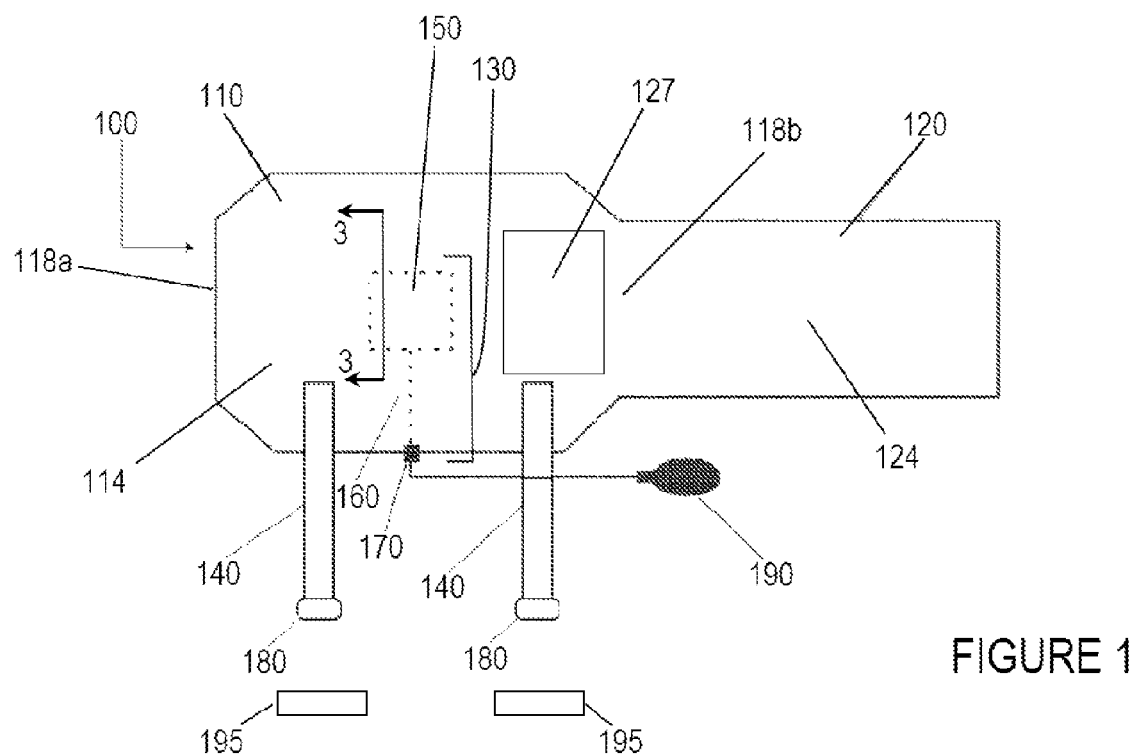
FIG. 1 illustrates a schematic view of the orthopedic system for reducing anterior shoulder dislocations in a patient.
Figure 2:
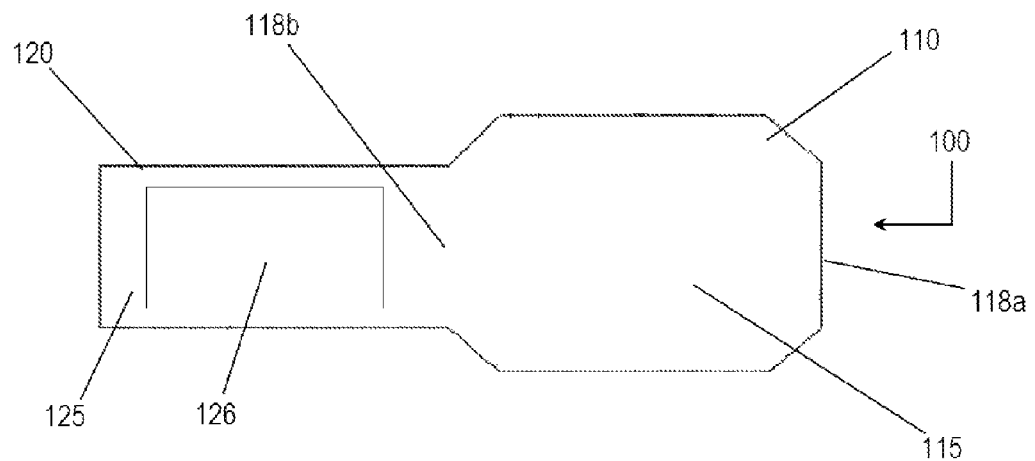
FIG. 2 illustrates an opposing side view of the humeral cuff and elongated band depicted in the system of FIG. 1.
Figure 3:
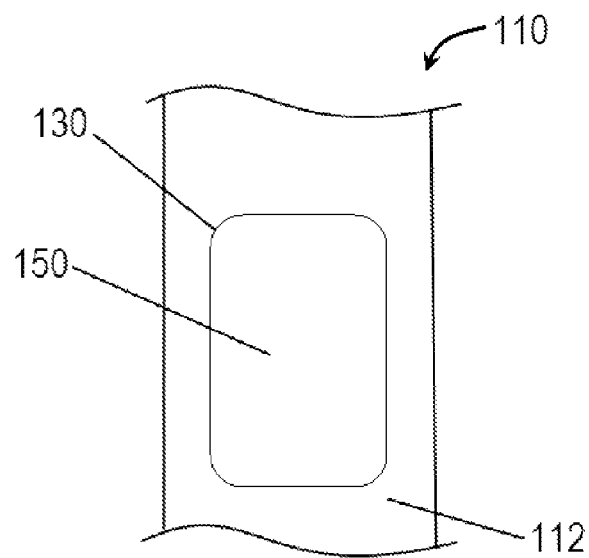
FIG. 3 illustrates a partial cross-sectional view of the humeral cuff of the system of FIG. 1.

Referring to FIG. 1, a system 100 is shown for reducing anterior shoulder dislocations in a patient, the apparatus of the system comprising a humeral cuff 110, an inflatable bladder 130, means for selectively inflating the inflatable bladder 190, and at least one elongated belt 140. In one aspect, the humeral cuff 110 has an overall length and width sufficient to surround a select portion of the patient's arm. It is contemplated that the humeral cuff 110 can be made of many suitable resilient fabrics or materials that yield to bending or folding, so that it can encircle a patient's upper arm and apply a slight amount of circumferential pressure to the upper arm. For example and without limitation, the humeral cuff 110 can be comprised of leather, nylon, polyester, cotton, a polyester cotton blend, neoprene, canvas, or other suitable pliable material.

In one embodiment, the humeral cuff 110 comprises an inner face 115 and defines an internal compartment 112. In this aspect, the humeral cuff 110 can be configured to selectively substantially surround a select portion of an arm of the patient in an operative position. In the operative position, the inner face 115 of the humeral cuff 110 has a first cross-sectional area which corresponds to the minimum cross-sectional area of the inner face of the humeral cuff while it is in the operative position.

In an exemplary aspect, and without limitation, the humeral cuff 110 can have a length of about approximately 10¾ inches and a width of approximately 8 inches. In another aspect, it is contemplated that the respective dimensions of the humeral cuff 110 can be varied based upon the size of the patient, taking into consideration factors including, but not limited to, age, weight, muscularity, and the like.

In another exemplary aspect, the internal compartment 112 can be configured to allow for easy access for cleaning. For example, and without limitation, at least a portion of the internal compartment 112 can comprise regions of loop fastener material. In another example, an opening can be defined therein the humeral cuff 110 such that the humeral cuff may be selectively opened to gain access to the internal compartment 112.

In one aspect, the humeral cuff 110 further comprises a pair of opposed end edges 118a, 118b and a means for selectively positioning the pair of end edges into the operative position in which the pair of end edges are positioned in select proximity or otherwise relative to each other so that the humeral cuff 110 substantially surrounds the select portion of the arm. As one will appreciate, the selective positioning of the pair of end edges 118a, 118b into the operative position can prevent the patient's arm from slipping through the humeral cuff 110. It is contemplated that the means for selectively positioning the pair of end edges into the operative position can comprise a variety of common attachment means, such as, for example and without limitation, stitching, adhesive bonding, stapling, snaps, buckles, Velcro, means known or used in the art for attaching resilient fabric or material, and the like.

In one specific aspect, the means for selectively positioning the pair of end edges into the operative position can comprise at least one elongated band 120 that terminates at one end edge of the pair of end edges 118a, 118b and has an inner surface 125. In this aspect, it is contemplated that the at least one elongated band can have a length of approximately 9 ¼ inches and a width of approximately 5 ¼ inches. Further, it is contemplated that the at least one elongated band 120 can be adjustable so that the humeral cuff 110 substantially surrounds the select portion of the arm. In an exemplary aspect, at least a portion of the at least one elongated band 120 can comprise a Velcro-type surface. In this aspect, it is contemplated that at least a portion of the inner surface 125 of the at least one elongated band 120 can comprise a Velcro-type receiving surface or loops 126 and at least a portion of the outer surface 114 of the humeral cuff 110 can comprise Velcro-type hooks 127 that are configured to engage and attach to a Velcro-type receiving surface or loops. In one exemplary aspect, and without limitation, the Velcro-type receiving surface or loops 126 of the at least one elongated band 120 can cover an area having a length of approximately 8 inches and a width of approximately 4 inches, and the Velcro-type hooks 127 positioned thereon the humeral cuff 110 can cover an area having a length of approximately 4 inches and a width of approximately 4 inches.

In a further aspect, the at least one elongated band 120 can comprise an outer surface 124 having a Velcro-type receiving surface or loops and Velcro-type hooks located adjacent to the Velcro-type loops on the outer surface of the at least one elongated band. In this aspect, the end edge of the humeral cuff 110 that opposes the at least one elongated band 120 can be attached to a transversely extending flexible strip of material to define a loop of material that is configured to threadably accept the at least one elongated band. In this aspect, and as one skilled in the art will appreciate, the at least one elongated band 120 can be threaded through the loop and folded back upon itself to engage and attach to the Velcro-type hooks 127 of the outer surface 114 of the humeral cuff 110.

In one aspect, the at least one elongated band 120 can comprise a plurality of elongated bands positioned relative to each other so that if one of the bands becomes unintentionally unfastened at least one remaining band will maintain a grip on the patient's upper arm in the same fashion as the first band. In one particular aspect, the plurality of elongated bands 120 can comprise a pair of elongated bands that are positioned substantially parallel to each other. In another aspect, the at least one elongated band can comprise one elongated band, which can allow for the humeral cuff 110 to be wrapped readily around the patient's upper arm. In a further aspect, the at least one elongated band 120 can narrow in width to form an edge, creating a taper.

In one aspect, an inflatable bladder 130 is mounted therein at least a portion of the internal compartment 112 of the humeral cuff 110. It is contemplated that the inflatable bladder 130 can be permanently or removably mounted therein the internal compartment 112 of the humeral cuff 110. In a further aspect, the inflatable bladder 130 can comprise a main chamber portion 150 and an integrally formed hose 160 with a barbed nipple connector 170 at its distal end, the hose open to the interior of the main chamber portion where it joins therewith. In another aspect, the inflatable bladder 130 can be made from an inflatable rubber material. Optionally, the inflatable bladder 130 can be flexible or foldable and can be inserted into and removed from the internal compartment 112 of the humeral cuff 110 through an opening. As one will appreciate, in one exemplary non-limiting example, when the inflatable bladder 130 is positioned within the internal compartment 112 of the humeral cuff 110, the centerline of the inflatable bladder can be positioned to lie roughly along the imaginary centerline of the humeral cuff, and the hose 160 can selectively extend out from the internal compartment through the opening as needed.

In this aspect, the means for selectively inflating the inflatable bladder 190 can be in select fluid communication with the inflatable bladder 130 such that the inner face 115 of the humeral cuff 110 can be selectively moved therefrom the operative position to an inflated position in which the inner face of the humeral cuff has a second cross-sectional area that is smaller than the first cross-sectional area which corresponds to the minimum cross-sectional area of the inner face of the humeral cuff while it is in the inflated position. The means for selectively inflating the inflatable bladder 190 can comprise, for example and without limitation, an inflation bulb, an air pump, an air compressor, and the like. As one will appreciate, in operation, the means for selectively inflating the inflatable bladder will comprise a source of pressurized gas. As one will further appreciate, inflation of the inflatable bladder 130 secures the humeral cuff 110 in place and prevents slippage of the humeral cuff.

In a further aspect, the at least one elongated belt 140 is attached to the humeral cuff 110. In one exemplary and non-limiting example, it is contemplated that the at least one elongated belt 140 can be made out of a resilient material that is not prone to elongate under stress. In one aspect, the at least one elongate belt 140 can comprise a thick nylon material that resists stretching and degradation due to liquids or other foreign substances. The at least one elongate belt 140 can be configured to be selectively coupled to a weight 195. Further, the at least one elongate belt 140 can be of an adjustable length and can comprise means for selectively adjusting the length of the at least one elongate belt.

The at least one elongate belt 140 can be formed into one or more descending loops. The at least one elongate belt 140 can have a top portion that is attached to the humeral cuff 110. The at least one elongate belt 140 and the humeral cuff 110 can be attached together using methods such as, without limitation, stitching, adhesive bonding, stapling, detachable snaps, Velcro type surfaces, or other means commonly known or used in the art for attaching resilient fabric or material. In one aspect, the at least one elongate belt 140 and the humeral cuff 110 can be stitched together using a resilient thread, so as to prohibit undesired movement between the at least one elongate belt and the humeral cuff. The at least one elongate belt 140 can have a bottom portion that is folded over onto itself to create a loop 180, which defines and encircles a space within the loop. The loop 180 can define a space that is capable of securing a ring or loop. The loop 180 can be made of any conventional weight-bearing materials, for example and without limitation, metal or plastic, and the like. The bottom portion of the at least one elongate belt 140 can be closed, affixing the loop 180. The bottom portion of the at least one elongated belt 140 forming the loop 180 can be closed by, without limitation, means of stitching, adhesive bonding, stapling, or many other means commonly known or used in the art of attaching one length of a belt to another length of a belt. In another aspect, the humeral cuff 110 can have at least one elongated belt 140 securing a loop 180. In a further aspect, two elongated belts can be attached to the humeral cuff 110.

In an additional aspect, an extender can be used to attach and support the weights 195 applied to the loop 180. In one aspect, the weights 195 can comprise a disk weight having a centrally located hole. As one will appreciate, this type of one or more weights would be most commonly used with weight training equipment and used on a weight bar in conjunction with other weights of various weights. The extender can have a central elongated shaft, with a top curved hook shaped end, and a bottom L-shaped end. The central elongated shaft can be constructed out of metal or many other types of resilient material capable of supporting a pulling force of at least up to the maximum weight to be used with this system. As one will appreciate, while the elongated shaft of the extender can be flexible, the top end and bottom end of the extender should remain rigid to properly support the pulling force of the weights placed upon it.

The curved hook end can have a diameter that allows the end to be placed through the loop 180, so that the extender and the weights 195 placed upon it will hang from and be supported by the loop. A plurality of extenders can be used with the humeral cuff 110, if a plurality of looped elongated belts 140 and a plurality of loops 180 are available on the humeral cuff. The extender can provide an L-shaped end to receive weights 195, but the extender can also be constructed so that the weight of the extender itself provides the necessary weight for the system.

In another aspect, the at least one elongate belt 140 can be folded over onto itself to create loop 180, which defines and encircles a space within the loop. In this aspect, the loop 180 can define a space that is capable of receiving weights 195, for example but not limited to the bulbous end of a dumbbell. In the example of a dumbbell, the dumbbell can be comprised of two weighted bulbous ends that are spaced apart from each other by a rigid hand grip, where the hand grip has a circumference less than that of either bulbous end. As one will appreciate, when using a dumbbell as the weights 195, the width of the at least one strap or belt should be approximately that of a hand grip of a dumbbell with the width of the belt not exceeding the length of the hand grip of the dumbbell.

In a further aspect, the at least one elongate belt 140 can be folded back onto itself (180 degrees) more than one time to create a plurality of loops, which define and encircle a space within each of the loops. The plurality of loops defines and encircles an area that can accommodate receiving weights 195, for example the bulbous end of a dumbbell. In the example of a dumbbell, as one will appreciate, the width of the belt or strap used to form the plurality of loops should be no greater than the length of the hand grip of the dumbbell that it is intended to receive. The ends of each of the plurality of loops can be attached together to define a closed loop end, with the closed loop ends of any loop of the plurality of loops attached to each other, so that the folds defining the closed loop ends are adjacent to one another. The loop closed ends can be closed by, without limitation, means of stitching, adhesive bonding, stapling or many other means commonly known or used in the art of attaching one length of a belt or strap to another length of a belt or strap.

At the point where the loop closed ends are attached together, the humeral cuff 110 can be affixed thereto using many common attachment means to permanently affix the humeral cuff to the loop closed ends. It is contemplated that once the dumbbell is placed into the space defined by a loop or the plurality of loops, the bulbous ends of the dumbbell can protrude outward from either side of the belt or strap defining the loop. As one will appreciate, the larger circumference of the bulbous end, relative to the narrow hand grip, will prevent sideway slippage of the dumbbell through the loop, so that the dumbbell will remain securely held within the loop.

In use, and referring to FIG. 1, a system of using the apparatus of the present invention comprises at least one weight 195 configured to selectively couple to at least a portion of the at least one elongated belt 140. As one will appreciate, the selective coupling of the at least one weight 195 to the at least a portion of the at least one elongated belt 140 allows for the application of downward gravitational force to the affected arm.

In operation, and referring to FIG. 1, a method of using the system of the present invention comprises positioning the patient in a substantially prone position, using the system on an upper portion of the affected arm of the patient, selectively positioning the humeral cuff 110 so that the humeral cuff substantially surrounds a select portion of the affected arm, and attaching at least one weight 195 to the at least one elongated belt 140 such that the gravitational force of the at least one weight pulls the arm downwardly relative to the torso of the patient. Positioning the patient in a substantially prone position comprises positioning the patient's affected arm such that the affected arm extends outwardly from the torso of the patient. In one aspect, the step of positioning the patient in a substantially prone position can comprise positioning a patient's torso horizontally on, without limitation, a table, bed, or similar piece of furniture such that the patient's affected arm hangs freely over the edge of the table, bed or similar piece of furniture. As one will appreciate, adjustable lengths of the at least one elongated belt 140 allow the at least one elongated belt to accommodate the length of the patient's affected arm, thereby maximizing the directional pull of the weights 195 by preventing the weights from contacting a floor or other surface.

In another aspect, the step of attaching at least one weight 195 to the at least one elongated belt 140 can comprise incrementally loading a plurality of weights thereto the at least one elongated belt. As one will appreciate, the incremental loading of weight to the at least one elongated belt can enable a health professional to determine the total amount of weight needed to apply the appropriate level of force to the patient's affected arm. In this aspect, the total weight attached to the at least one elongated belt can be between about 1 and 50 pounds, preferably between about 5 and 35 pounds, and more preferably between about 10 and 25 pounds. As one will appreciate, the amount of weight attached to the at least one elongated belt will be dependent on, without limitation, the type of injury reported by the patient, the size and musculature of the patient, and the duration of the time that the weights 195 are directionally applying a force to the patient's affected arm. In a further aspect, the patient can be positioned in the substantially prone position for between about 1 and 60 minutes, preferably between about 5 and 45 minutes, and more preferably between about 10 and 30 minutes. As one will appreciate, the length of time during which the patient will be exposed to the forces of the weights 195 can vary depending on, without limitation, the severity of the patient's anterior shoulder dislocation, the amount of weight applied, and other factors.

In another aspect, the method of using the system of the present invention can further comprise selectively relaxing at least a portion of the patient's muscles. For example, and without limitation, the patient can be instructed to relax his or her muscles during the use of the method. In a further aspect, the method of using the system of the present invention can further comprise selectively administering pain medication to the patient. As one will appreciate, the application of downward force to the affected shoulder of the patient can cause intense pain in the patient, and the administration of pain medication to the patient can help the patient tolerate the pain. In still a further aspect, the method of using the system of the present invention can further comprise manipulation of the patient's scapula such that shoulder dislocation in the affected arm is reduced. As one will appreciate, the use of scapular manipulation of the affected arm of the patient in conjunction with downwardly pulling the affected arm of the patient can effectively reduce anterior shoulder dislocations in the patient. It is contemplated that the method of the present invention can be used in conjunction with other known techniques for reducing anterior shoulder dislocations.

Though not wishing to be bound by any particular theory, the method of the present invention utilizes the force of gravity to cause the weights 195 to be urged in the direction of pull through the center of the upper arm. Therefore, the direction of pull is directly downward from the main mass of the upper arm and the patient's shoulder. No means is provided to allow or require a patient to grip anything with their hand or support any weight with the forearm, so that a minimum of muscular stress is required to use this apparatus. As one will appreciate, with the direction of pull being applied to the upper arm, the direction of pull is acting on the shoulder area of the person, as opposed to involving the elbow, forearm, wrist or hand. As one will further appreciate, there is no effort required on the part of the patient to hold onto or maintain the attachment of the orthopedic apparatus to the patient's upper arm, since the at least one elongated band 120 and inflatable bladder 130 securely hold the humeral cuff in place. The present invention can be used for patients who cannot hold or tolerate a weight in the lower portion of the arm or hand. For example, and without limitation, the present invention can be used in a patient with a broken ulna, radius, hand, wrist or finger, in a patient with a missing or bandaged lower arm, wrist, hand or finger, or in an unconscious, sedated, drugged or mentally incapacitated patient.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A system for reducing anterior shoulder dislocations in a patient, the system comprising:
    a humeral cuff defining an internal compartment, wherein the humeral cuff is configured to selectively substantially surround a select portion of an arm of the patient;
    an inflatable bladder mounted therein the internal compartment of the humeral cuff;
    at least one elongated belt connected to the humeral cuff; and
    at least one weight configured to selectively couple to at least a portion of the at least one elongated belt.

2. The system of claim 1, wherein the humeral cuff further comprises:
    a pair of opposed end edges; and
    means for selectively positioning the pair of end edges into an operative position in which the pair of end edges are positioned in select proximity to each other so that the humeral cuff substantially surrounds the select portion of the arm.

3. The system of claim 2, wherein the humeral cuff has an inner face, and wherein, in the operative position, the inner face of the humeral cuff has a first cross-sectional area.

4. The system of claim 3, further comprising means for selectively inflating the inflatable bladder such that the inner face of the humeral cuff, when positioned in the operative position, is urged inwardly to an inflated position in which the inner face of the humeral cuff has a second cross-sectional area that is smaller than the first cross-sectional area.

5. The system of claim 2, wherein the humeral cuff comprises at least one elongated band that terminates at one end edge of the pair of end edges, and wherein the at least one elongated band has an inner surface.

6. The system of claim 5, wherein at least a portion of the inner surface of the at least one elongated band comprises a region of loop fastener material.

7. A method for reducing anterior shoulder dislocations in a patient having a torso and an affected arm, the method comprising:
    positioning the patient in a substantially prone position such that the affected arm of the patient extends outwardly from the torso of the patient;
    providing a system comprising:
        a humeral cuff comprising a pair of opposed end edges and defining an internal compartment;
        an inflatable bladder mounted therein the internal compartment of the humeral cuff;
        at least one elongated belt connected to the humeral cuff; and
        at least one weight;
    selectively positioning the pair of end edges of the humeral cuff into an operative position in which the pair of end edges are in select proximity to each other so that the humeral cuff substantially surrounds a select portion of the affected arm; and
    attaching at least one weight to at least one elongated belt such that the gravitational force of the at least one weight pulls the affected arm downwardly relative to the torso of the patient.

8. The method of claim 7, wherein the step of attaching at least one weight to at least one elongated belt comprises incrementally loading a plurality of weights thereto the at least one elongated belt.

9. The method of claim 7, wherein the step of attaching at least one weight to at least one elongated belt comprises loading a total weight of between about 10 and 25 pounds.

10. The method of claim 7, wherein the patient is positioned in the substantially prone position for between about 10 and 30 minutes.

11. The method of claim 7, further comprising selectively relaxing at least a portion of the patient's muscles.

12. The method of claim 7, further comprising selectively administering pain medication to the patient.

13. The method of claim 7, further comprising manipulating the patient's scapula such that the shoulder dislocation in the affected area is reduced.

14. The method of claim 7, wherein the humeral cuff has an inner face, and wherein, in the operative position, the inner face of the humeral cuff has a first cross-sectional area, the method further comprising, after positioning the humeral cuff in the operative position, selectively inflating the bladder such that the inner face of the humeral cuff is urged inwardly to an inflated position in which the inner face of the humeral cuff has a second cross-sectional area that is smaller than the first cross-sectional area.

* * * * *